United States Patent [19]
Walsh et al.

[11] Patent Number: 5,539,649
[45] Date of Patent: Jul. 23, 1996

[54] AUTOMATED DESIGN AND MANUFACTURE OF ARTIFICIAL LIMBS

[75] Inventors: Nicolas Walsh; Virgil Faulkner; Keith S. Pickens; Mark V. Muller, all of San Antonio; Henry L. Grothues, Bulverde, all of Tex.

[73] Assignee: Southwest Research Institute, San Antonio, Tex.

[21] Appl. No.: 373,866

[22] Filed: Jan. 17, 1995

Related U.S. Application Data

[63] Continuation of Ser. No. 15,171, Feb. 10, 1993, abandoned.
[51] Int. Cl.⁶ .................................................... G06F 19/00
[52] U.S. Cl. ........................... 364/474.05; 364/474.24; 623/901
[58] Field of Search ............... 128/660.01, 661.01; 364/474.04, 474.05, 474.03, 468, 506, 474.24, 474.25; 623/901

[56] References Cited

U.S. PATENT DOCUMENTS

| | | | |
|---|---|---|---|
| 4,436,684 | 3/1984 | White | 264/138 |
| 4,575,805 | 3/1986 | Moremann et al. | 364/474.05 |
| 4,742,464 | 5/1988 | Duret et al. | 364/474.05 X |
| 4,821,200 | 4/1989 | Öberg | 364/474.24 |
| 4,995,087 | 2/1991 | Rathi et al. | 364/474.08 X |
| 5,031,120 | 7/1991 | Pomerantz et al. | 364/474.24 X |
| 5,092,022 | 3/1992 | Duret | 364/474.05 X |
| 5,121,334 | 6/1992 | Riley et al. | 364/474.05 |
| 5,269,309 | 12/1993 | Fort et al. | 128/661.01 |
| 5,293,326 | 3/1994 | Arima et al. | 364/506 |
| 5,448,489 | 9/1995 | Reuben | 364/474.05 |

*Primary Examiner*—Roy N. Envall, Jr.
*Assistant Examiner*—Brian C. Oakes
*Attorney, Agent, or Firm*—Gunn, Lee & Miller

[57] ABSTRACT

The system for automated design and construction of artificial limb sockets for amputees consists of an array of ultrasound transducers especially constructed to insonify the residual limb of an amputee. The time-of-flight information recovered from this procedure is then stored in a computer, where it can be processed to provide dimensional information with regard to the relative location of the limb, skin, and bone surfaces in space. This three dimensional information is then used to produce an image of the limb with a computer aided design system for customized prosthetic design and manufacture.

7 Claims, 6 Drawing Sheets

AUTOMATED DESIGN AND MANUFACTURE OF ARTIFICIAL LIMBS

This is a continuation of application Ser. No. 08/015,171 filed on Feb. 10, 1993, now abandoned.

FIELD OF THE INVENTION

This invention relates generally to improvements in apparati for forming artificial limb sockets, and more particularly, to an automated system for using ultrasound imaging techniques in conjunction with computer aided design and manufacture of artificial limb sockets, so that such objects can be designed and produced quickly, accurately and inexpensively.

BACKGROUND

It is common practice in the design and manufacture of artificial limbs to take plaster impressions of the affected limb, and to make a positive plaster model from the impression. This process of measurement and construction is not very accurate, or repeatable, and the artificial limb maker (prosthetist) is given no information on the exact location of the bone within the limb tissue. However, it is the location of the bone and its relation to the limb tissue which determines the final shape of the artificial limb socket, since the bone and tissue are used to help support the artificial limb on the amputated stump. The primary limitations impeding a good fit are the high cost associated with each test fit and the skill level required by the artificial limb maker. Many trial sockets may be required to provide a comfortable fit for an amputee with cost being proportionate to the number of fittings.

In recent years, several attempts have been made at automating the artificial limb design and manufacturing process, but none characterize the location of the bone in relation to the limb tissue. This results in an ineffective and usually painful fit for the artificial limb socket to the amputee, and, as a consequence, the socket is discarded. In addition, there is no complete system that both accurately and automatically measures the limb and provides a direct interface to a numerically controlled milling machine for the artificial limb socket manufacturer. Finally, the current process provides no way of conveniently saving the results of the final prosthetic socket model. The current process produces a plaster model that is destroyed as pan of the artificial limb socket construction process. Thus, when the original socket becomes worn or ill-fitting with use (the amputee's stump normally changes size and shape as tissues shrink during the first few years of wearing a prosthesis) and a new socket is necessary, the process must start all over from an initial plaster impression.

There continues to be a need for rapid design and production of artificial limbs, because in the United States alone there are approximately 50,000 limb amputations performed every year. Therefore those concerned with the rehabilitation of these people have often requested a more rapid, reliable and economical system for the design and manufacture of artificial limbs. The method and apparatus of the present invention, discussed in greater detail below, clearly fulfills those needs.

SUMMARY OF THE INVENTION

The present invention provides a new and improved system for designing and manufacturing artificial limbs by utilizing ultrasound and a computer to generate a three dimensional exact duplicate of the amputee's stump (residual limb). In the presently preferred embodiment, by way of example and not necessarily by way of limitation, this invention uses the principles of computer generated graphics in combination with ultrasound to execute computer aided design (CAD) and computer aided manufacturing (CAM) off artificial limbs from computer instructions. This invention can be applied for the purposes of designing and sculpturing models and prototypes in a design phase of artificial limb socket development, as a manufacturing system, or as a pure art form. This invention provides a method for making artificial limbs or other solid objects and consists of two parts, (1) the ultrasound scanner, and (2) the computer control and data acquisition system.

The present invention satisfies a long existing need for a CAD/CAM system capable of quickly, accurately, and inexpensively designing and fabricating artificial limbs. The above and other advantages of this invention will be apparent from the following more detailed description when taken in conjunction with the accompanying drawings and illustrative embodiments.

DETAILED DESCRIPTION OF THE PREFERRED EMBODIMENT

Figure 1:
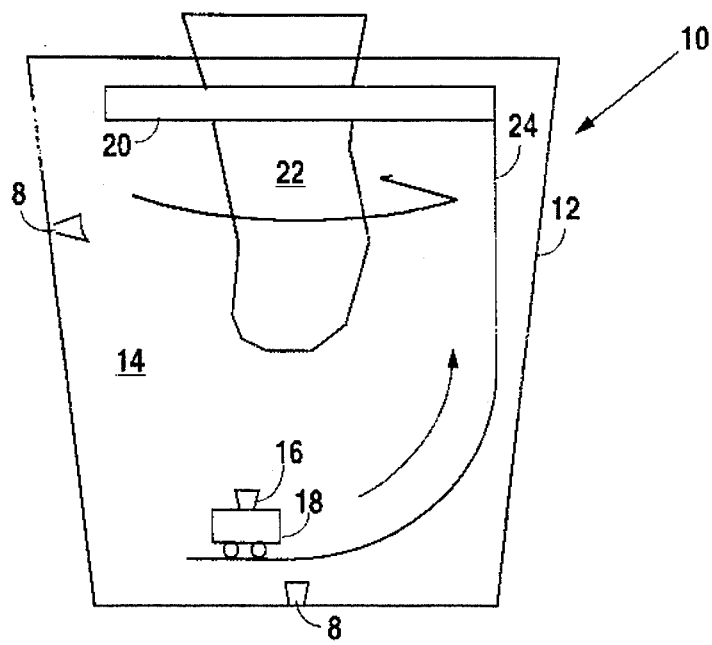
FIG. 1 is an elevational side view of the automated mapping system used in the present invention.

The system for obtaining information necessary for the automated design and manufacture of a prosthesis is shown generally in FIG. 1. The system 10 comprises a tank 12 containing an ultrasonic transmitting medium 14 in which ultrasonic pulses or echoes may be transmitted and detected by ultrasonic transducers 16 carried on a movable cart 18. A carriage assembly 20 provides a means to allow both horizontal and vertical rotation of the transducers around the surface of the amputee limb or other object 22 which is to be mapped. The cart 18 containing the array of ultrasonic transducers is moved along a curved track 24 while directing ultrasound signals toward the object 22. As the cart 18 traverses the curved track 24, it is stopped at different elevations so that it can be used for radial scanning of the object, via rotation of the carriage assembly. In this manner, through a series Of actual radial movements, the object 22 can be fully insonified. The ultrasound transducers 16 are electrically excited to transmit ultrasound waves and also are, used to receive the return echoes from the limb 22 and its skeletal structure. Several ultrasonic transducer units 8 are located at fixed positions within the tank to provide a baseline indication of the initial (pre-scan) limb location. Although ultrasound is used in the preferred embodiment, alternate embodiments of the present invention can employ various types of electromagnetic radiation, including beams of light, x-rays, electron beams, or high energy particles.

Figure 2:
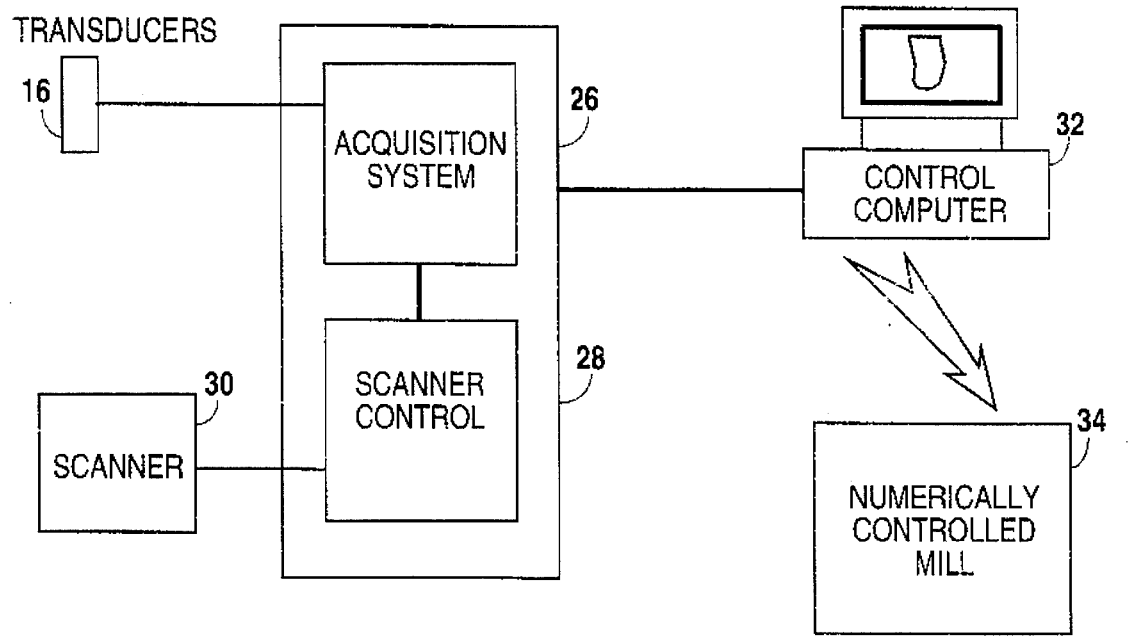
FIG. 2 is a schematic block diagram of the system for using information provided by the transducers in FIG. 1 to control the manufacture of a prosthesis.

The data acquisition and scanner control system used in the present invention is shown generally in FIG. 2. The acquisition and control system is used to direct the scanner movement and multiplex the electrical signals to the ultrasonic array in a cyclic fashion. The ultrasound signal transit times are processed and formatted by the control computer so as to produce a three dimensional image of the object in space for display and manipulation by computer aided design systems. The resulting CAD data base is used to design the prosthetic socket or other objects and drive a numerically controlled milling machine for their manufacture. This data base can be saved for future use when the amputee's socket becomes worn with use, and it is necessary to produce a new socket for the artificial limb.

Referring to FIG. 2, signals received from the transducers 16 are provided as input signals to the acquisition system 26 which comprises electrical circuitry well known in the art. The scanner system illustrated generally by reference numeral 30 is controlled by a scanner control module 28, which also uses control mechanisms and circuitry which are known in the art. The control computer 32, which is connected to the acquisition and control system via an appropriate data link, is used to process data received from the transducers and to provide control signals to the scanner control module. Dam processed by the control computer 32, using a series of algorithms discussed in greater detail below, is used to operate a numerically controlled mill (or other CAM equipment) for automatic production of a prosthetic device.

Figure 3A:
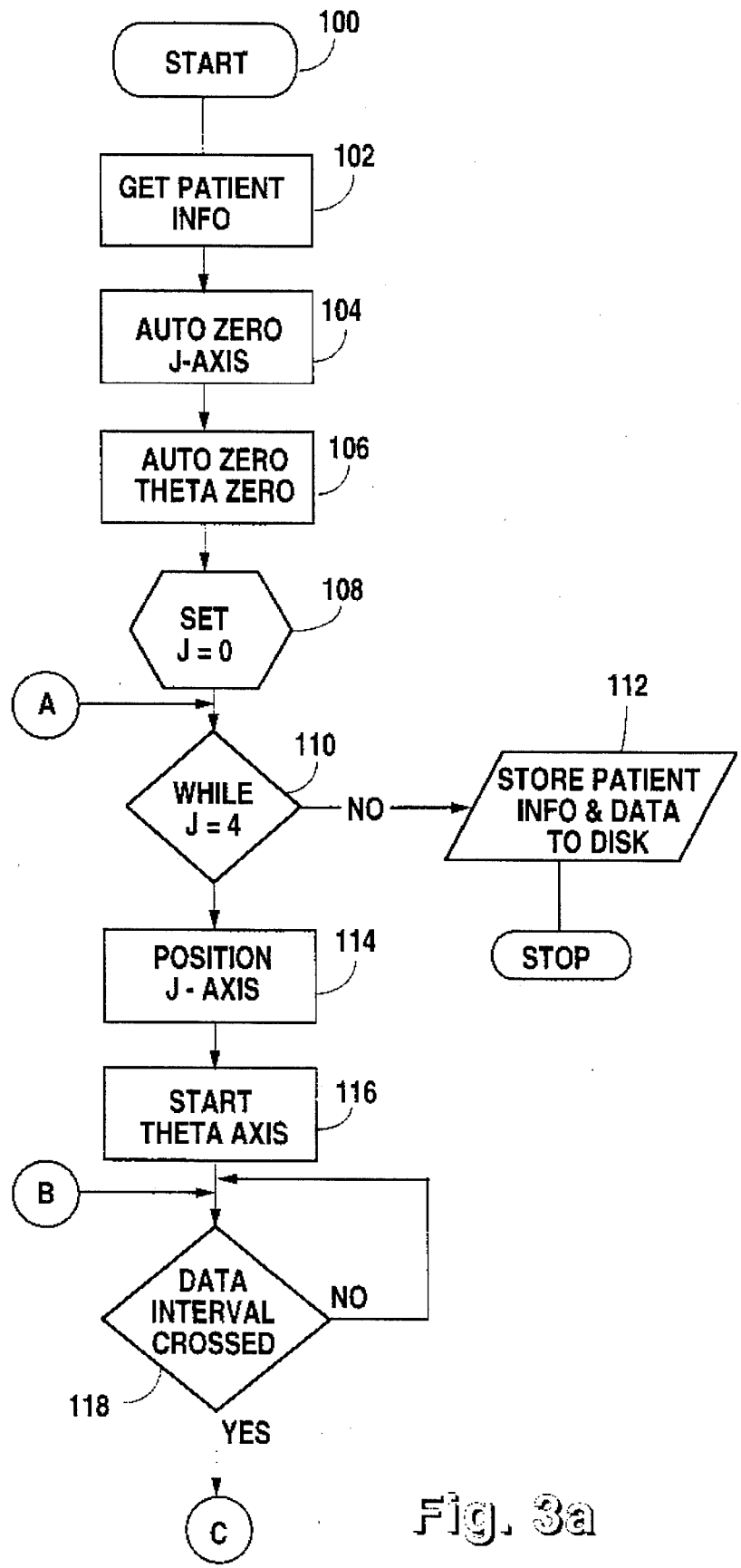
FIGS. 3a, 3b, 3c, 3d and 3e are a flow chart illustration of the processing steps for implementing the method of the present invention.
Figure 3B:
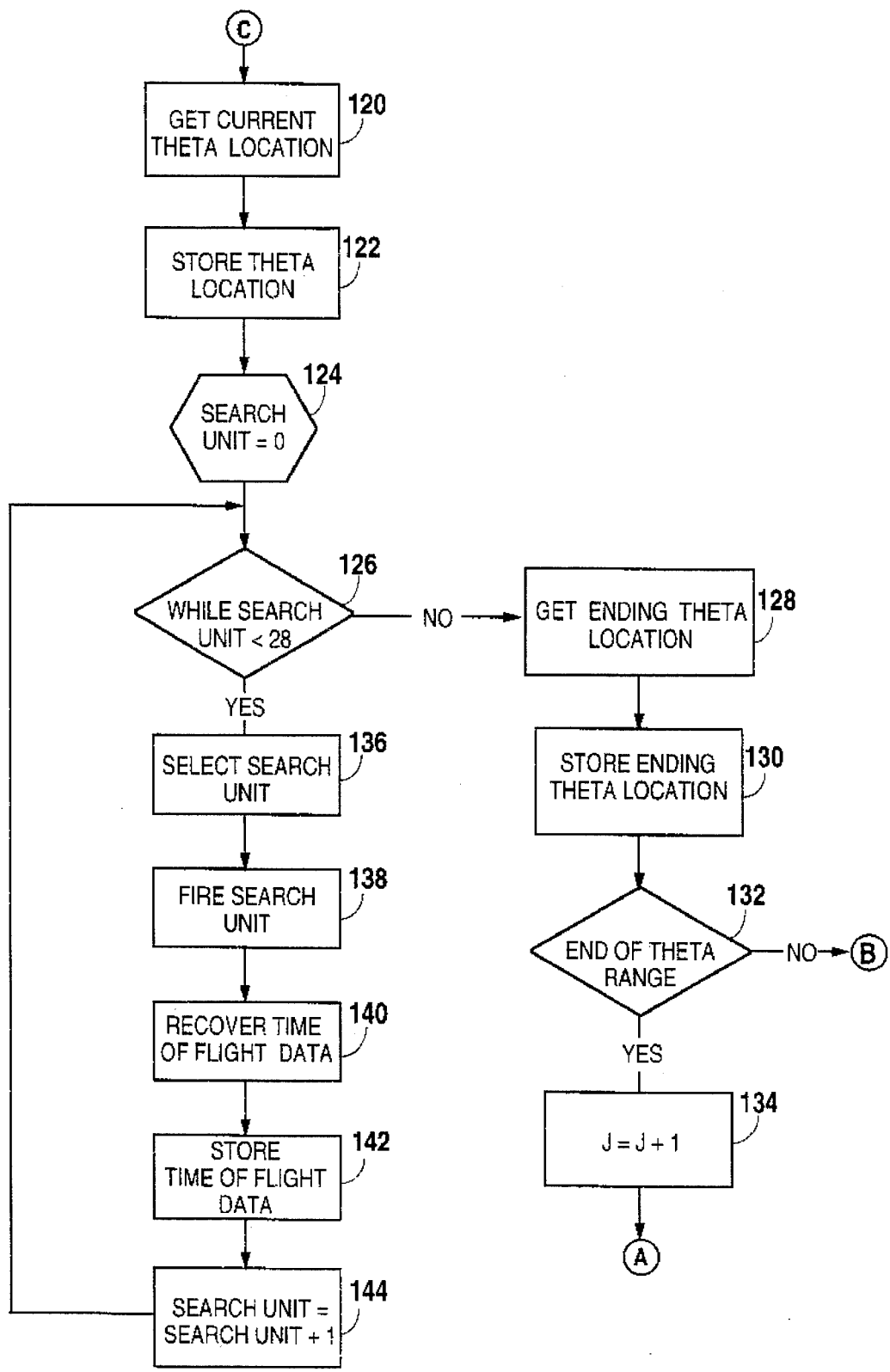

FIGS. 3a–b provide a sugary of the processing steps used to control the scanner portion of the system. In step 100 the system is started and patient information is entered into the system in step 102. In steps 104 and 106, the system provides an automated zero position reference for the j axis and the them axis, respectively. In step 108, a counter for the j axis is set equal to zero, and in step 110, the system performs a test on the value of the j index to determine if this index is less than four. If the system determines that the index is not less than four, the patient information and data is stored to disk in step 112. However, if the j index is less than four, the position is set for the j axis in step 114, and the system then starts the them axis rotational movement in step 116.

In step 118, a test is performed to determine whether a data interval has been crossed. If the answer to this test is "no," the system continues moving, and the test is run again. However, if the system determines that a data interval has been crossed, then the current them location is mad in step 120 and is stored in step 122. In step 124, the search unit counter is set equal to zero, and a test is performed in step 126 to determine whether the current value of the search unit counter is less than 28. If the answer to this test is "no," then the final them location is read in step 128 and stored in step 130. In step 132, a test is run to determine whether the end of the them range has been reached. If the answer to this test is "no," then the system returns to step 118. However, if the answer to this test is "yes," then the j index is incremented by one unit in step 134, and the system then returns to step 110. If the answer to the test performed in step 126 is "yes," then the search unit is selected in step 136 and "fired" (so as to emit ultrasound) in step 138. The time of flight data is recovered in step 140 and is stored in step 142. In step 144, the search unit counter is incremented by one, and the system then returns to step 126 to repeat the above discussed processing steps.

Figure 3C:
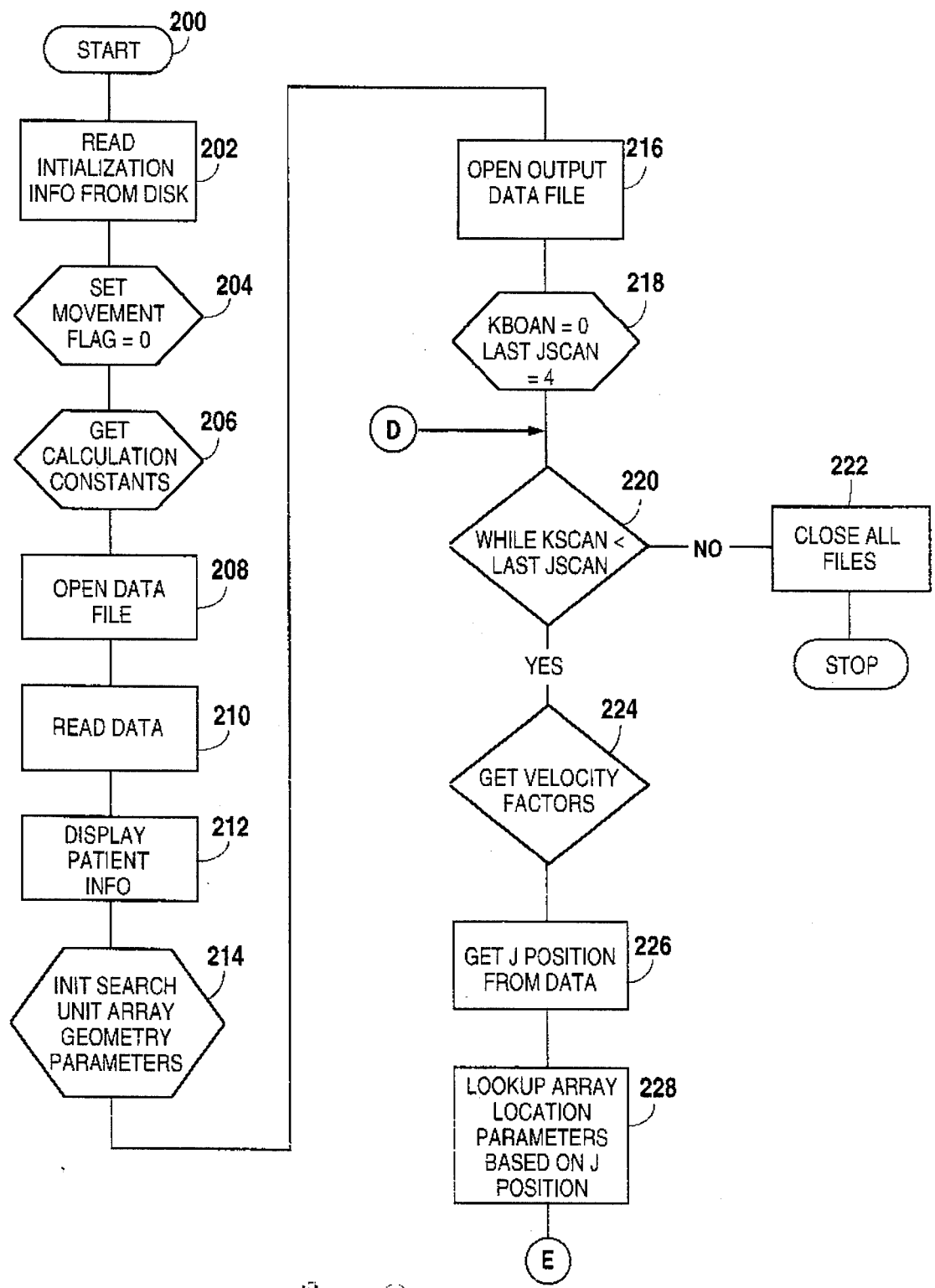
Figure 3D:
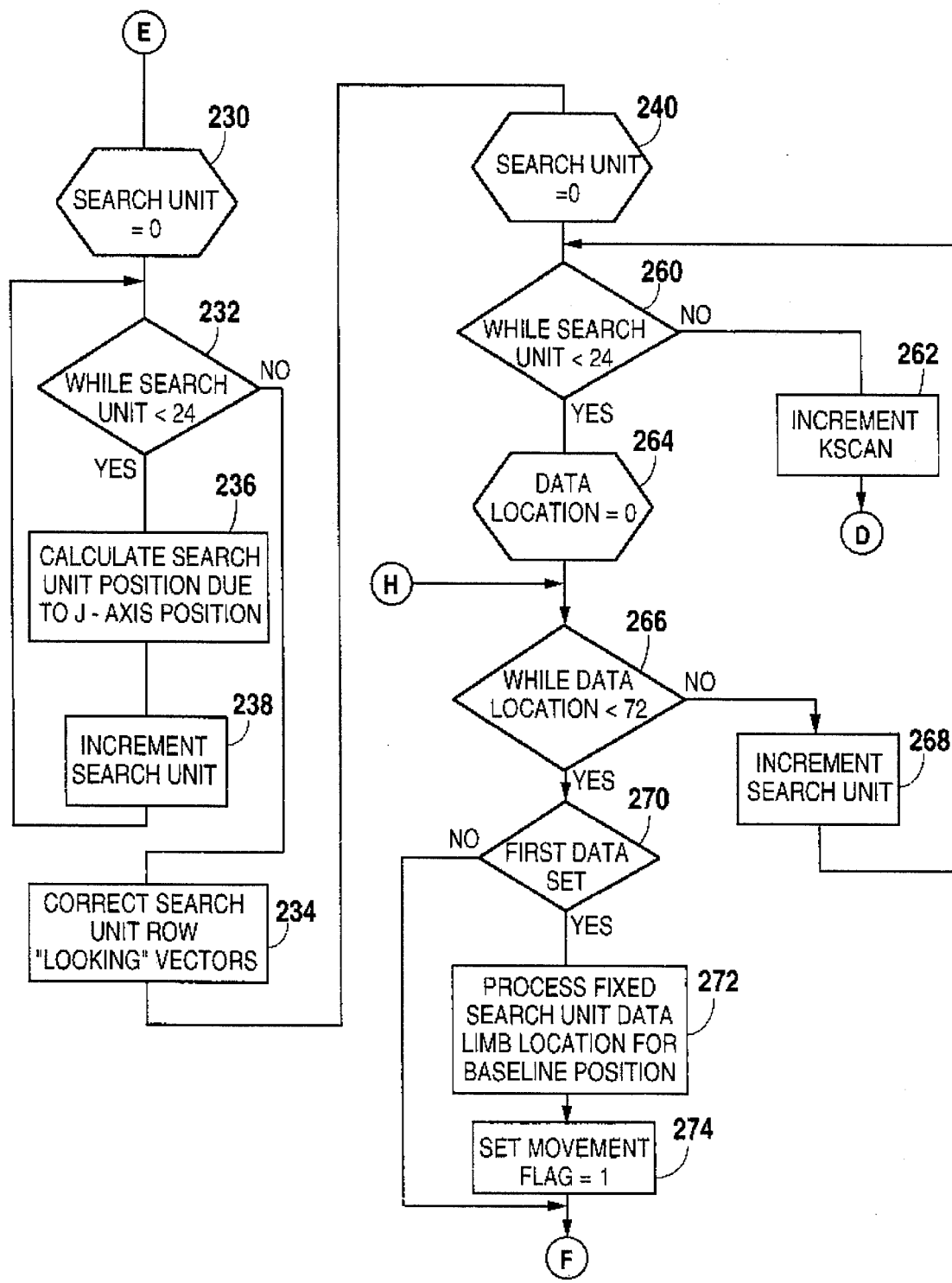
Figure 3E:
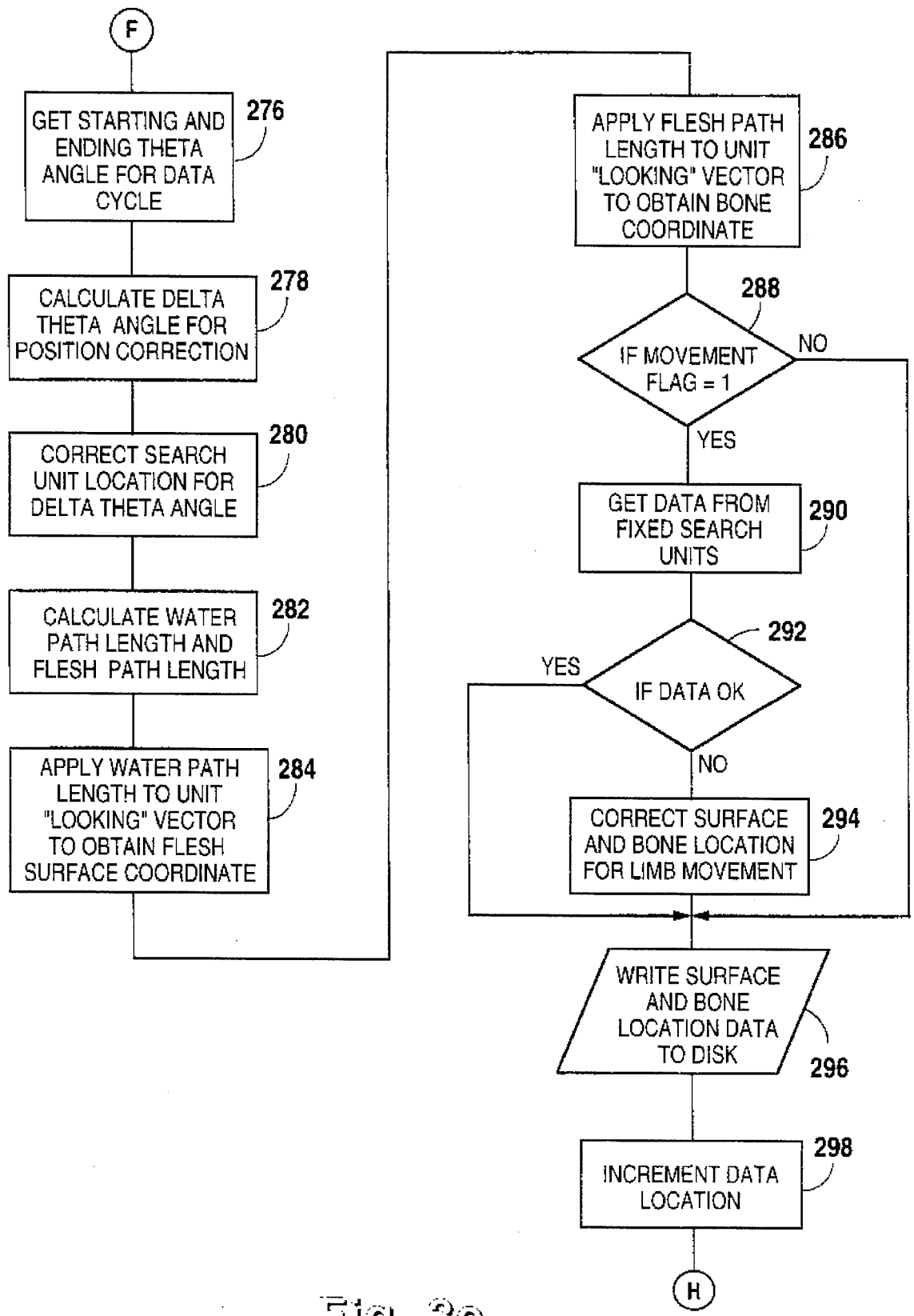

The processing steps relating to the image display are shown generally in FIGS. 3c–e. In step 200, the processing is started, and in step 202, initialization information is read from the system disk drive. In step 204, a movement flag is set equal to zero, and calculation constants are set in step 206. In step 208, a data file is opened and the recorded data is then read in step 210. Information related to the patient is displayed by the system in step 212. In step 214, search unit array geometry parameters are initialized. In step 216, an output data file is opened. In step 218, the variable KSCAN is set equal to zero, and the variable LAST JSCAN is set equal to four. In step 220, the system determines whether the current value of KSCAN is less than the cam value of LAST JSCAN. If the answer to this test is "no," then all ties am closed in step 222. However, if the answer to this step is "yes," then the velocity factors are set in step 224. In step 226, the current value of the j position is react from the data filer, and in step 228, this value is used to look up array location parameters based on the j position.

In step 230, a search unit counter is set equal to zero, and in step 232, a test is run on the current value of the search unit counter. If the test performed in step 232 indicates that the value of the search unit counter is less than 24, then the system proceeds to calculate the search unit position in accord with its j axis position in step 236. In step 238, the search unit counter is incremented, and the system returns to step 232. If, however, the test performed in step 232 indicates that the current value of the search unit counter is greater than or equal to 24, then the system proceeds to step 234 where the system corrects the search unit row "looking" vectors.

In step 240, the search unit counter is reset to zero and in step 260 a test is again performed to determine whether the current value of the search unit counter is less than 24. If the answer to this test is "no," then the value of the variable KSCAN is incremented and the system returns to step 220. If, however, the answer to the test performed in step 260 is "yes," then the data location is set equal to zero in step 264. In step 266, a test is performed on the current value of the data location to determine if this value is less than 72. If the answer to this test is "no," then the search unit counter is incremented in step 268, and the system returns to step 260. If, however, the answer to the test performed in step 266 is "yes," then a test is performed in step 270 to determine whether the first data set has been obtained. If the answer to the test performed in step 270 is "yes," then the system proceeds to step 272 where the system processes fixed ultrasonic transducer unit data to determine a baseline position for limb location. In step 274, the movement flag is set equal to one, and the system proceeds to step 276 in which the starting and ending them angle for data cycle is read. If the answer to the test performed in step 270 is "no," then the system bypasses steps 272 and 274 and proceeds directly to step 276.

In step 278, the system calculates the delta them angle for position correction, and in step 280, the system corrects the search unit location for the delta theta angle. In step 282, water path length and flesh path length are calculated with this calculated value being applied to the unit "looking" vector to obtain surface coordinates. In step 284, the water path length is applied to the unit "looking" vector to obtain a flesh surface coordinate. In step 286, the flesh path length calculated in step 282 is applied to the unit "looking" vector to obtain a bone coordinate. In step 288, a test is performed to determine whether the movement flag is equal to one. If the answer to this test is "no," then the system immediately proceeds to step 295. However, if the answer to the test performed in step 298 is "yes," then the data is read from the fixed ultrasonic transducer units in step 290, and a test is performed in step 292 to determine whether the data is "ok" (i.e., within a range of reasonable values given the baseline limb position). If it is determined that the data is "ok," then the system proceeds to step 296. However, if the test performed in step 292 indicates that the data is not "ok," then the surface and bone location for limb movement is corrected in step 294. In step 296, the system writes the surface and bone location to disk and the data location is than incremented in step 298. The system then proceeds to step 266 to repeat the processing steps from steps 266 through 298.

The present invention is designed to use the principles of computer generated graphics combined with ultrasound to simultaneously execute computer aided design and computer aided manufacturing and to produce artificial limbs and other objects directly from computer instructions. This invention, referred to as the ultrasound prosthetic imaging device CUPID), can be used to sculpture models and to produce prototypes in the design phase of model development, manufacturing, or as an art form.

Many different types of object forms can be created with the system of the present invention. However, complex forms arc more easily created by using the functions of a computer to help generate the program commands and then transmit these commands to a numerically controlled milling machine for forming. It should be appreciated, however, that other forms of appropriate measurements such as a three dimensional digitizer, laser beams and video cameras may be used in the practice of this invention without departing from the scope and intent of the invention.

By way of example, in the conventional artisan process employed today for the design and manufacture of artificial limbs, the artificial limb maker creates a positive model made from plaster of paris. This model is derived directly from the amputee's limb. In this way, an artificial limb can be manufactured without the amputee being physically present. However, once the plaster cast is broken (as pan of the fabrication process), no record of the shape of the limb exists. Further fittings require the creation of a completely new cast, as well as another visit by the amputee. In addition, this method of construction provides no indication of the relative location of the bone position within the residual limb. It is the position of this bone which contributes greatly to the support structure of the prosthesis, and therefore bone location is important. The current method relies on He experience and tactile judgment of the prosthetist for proper molding of the cast to incorporate support of the limb and its internal structure.

The ultrasound apparatus of the present invention has many advantages over currently used apparatus for producing artificial limbs. This invention avoids the need of employing a highly skilled technical individual to perform the expensive, time consuming, laborious and artisan skill required of the present artificial limb maker. The designer can work directly with the computer, which provides permanently recorded data to document the limb shape and relative location of the internal bone structure. When he is satisfied with the prosthetic socket design displayed on the computer screen, he can then transmit this information to another location for socket manufacture. If after the socket is designed and manufactured, and the fit is not adequate, the present invention allows for accurate and rapid redesign and manufacture with the ability to reproduce exactly the last design. After the design is perfected, the prosthesis manufacturer can begin immediately to produce the limb without the normal waiting period of several weeks or even months, ultimately adding to the high production cost of today's artificial limbs.

Although the apparatus for the production of computer aided design and computer aided manufacture of artificial limbs of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

What is claimed is:

1. A system for producing a three-dimensional topographic image of a portion of a human limb and for producing a prosthetic device for attachment to said limb, comprising:

transducer means for generating an ultrasonic signal and for directing said ultrasonic signal toward said limb, said transducer further comprising means for detecting portions of said ultrasonic signals reflected by the surface of said limb and by the surface of the bone within said limb and for producing electronic signals in response thereto;

means for moving said transducer to a plurality of positions proximate to the surface of said limb;

means for tracking a source point in space of said ultrasonic signal;

data processing means for processing a plurality of said electronic signals from said transducer and information from said tracking means to produce an electronic data representation of said surfaces of said limb and said bone;

data modification means for defining a limb socket surface structure for said prosthetic device based on modification of said electronic data representation of said surface of said limb and according to said electronic data representation of said surface of said bone, said modification serving to provide optimal support structures to areas on said limb socket surface proximal to said bone; and a numerically controlled mill for automated production of said prosthetic device for attachment to said limb, said numerically controlled mill being responsive to control signals generated by said data processing means and said data modification means.

2. The system according to claim 1, further comprising means for visual display of a graphic representation of the topology of said surface of said limb, said bone, and said prosthetic device.

3. The system according to claim 2, further comprising archival data storage means for storing a multiplicity of said graphic representations.

4. The system according to claim 3, said system utilizing stereolithography techniques to produce said topographic image of said limb, said bone, and said prosthetic device.

5. The system according to claim 1, said transducer means comprising a multiplicity of individual transducers.

6. The system according to claim 1, further comprising a group of one or more stationary transducers, said group of stationary transducers providing electronic signal data used to eliminate movement artifacts from said electronic data representation of said surfaces of said limb and said bone.

7. The system according to claim 1, further comprising means for visual display of a graphic representation of the topology of said surface structure for said prosthetic device.

* * * * *